US012642949B2

(12) United States Patent
Fantuzzi et al.

(10) Patent No.: US 12,642,949 B2
(45) Date of Patent: Jun. 2, 2026

(54) HEMOSTATIC VALVE FOR MEDICAL DEVICE INTRODUCER

(71) Applicant: ABIOMED, Inc., Danvers, MA (US)

(72) Inventors: Glen R. Fantuzzi, Danvers, MA (US); Dion Mraz, Danvers, MA (US)

(73) Assignee: ABIOMED, Inc., Danvers, MA (US)

( * ) Notice: Subject to any disclaimer, the term of this patent is extended or adjusted under 35 U.S.C. 154(b) by 0 days.

(21) Appl. No.: 18/214,049

(22) Filed: Jun. 26, 2023

(65) Prior Publication Data

US 2023/0414916 A1     Dec. 28, 2023

Related U.S. Application Data

(63) Continuation of application No. 16/784,329, filed on Feb. 7, 2020, now Pat. No. 11,730,942, which is a continuation of application No. 15/245,982, filed on Aug. 24, 2016, now Pat. No. 10,576,258.

(60) Provisional application No. 62/209,288, filed on Aug. 24, 2015.

(51) Int. Cl.
*A61M 39/06*          (2006.01)
*A61M 25/06*          (2006.01)

(52) U.S. Cl.
CPC ........ *A61M 39/06* (2013.01); *A61M 25/0662* (2013.01); *A61M 39/0606* (2013.01); *A61M 25/0668* (2013.01); *A61M 2039/0626* (2013.01); *A61M 2039/064* (2013.01); *A61M 2039/066* (2013.01)

(58) Field of Classification Search
CPC ................................................ A61M 25/0668
See application file for complete search history.

(56) References Cited

U.S. PATENT DOCUMENTS

| | | | |
|---|---|---|---|
| 5,312,355 A | 5/1994 | Lee | |
| 6,551,283 B1 * | 4/2003 | Guo ...................... | A61M 39/06 251/149.1 |
| 6,712,791 B2 | 3/2004 | Lui et al. | |
| 7,241,276 B2 | 7/2007 | Argentine et al. | |
| 8,147,456 B2 | 4/2012 | Fisher et al. | |

(Continued)

FOREIGN PATENT DOCUMENTS

| | | |
|---|---|---|
| CN | 101808692 B | 9/2012 |
| CN | 203763666 U | 8/2014 |

(Continued)

OTHER PUBLICATIONS

Office Action from corresponding Japanese Patent Application No. 2021-163170 dated Aug. 14, 2023 (4 pp.).

(Continued)

*Primary Examiner* — Andrew Yang
(74) *Attorney, Agent, or Firm* — BOTOS CHURCHILL IP LAW LLP

(57) ABSTRACT

An introducer for insertion of a medical device into a patient's vasculature includes an elongate introducer body, a hub, and a hemostatic valve. The elongate introducer body includes a longitudinal axis, a proximal region, a distal region, and an inner lumen. The hub is coupled to the proximal region of the introducer body. The hemostatic valve is disposed within the hub and forms a liquid-tight seal across the inner lumen. The introducer includes a guide configured to guide an object towards the center of the valve during insertion of the object.

13 Claims, 8 Drawing Sheets

(56) References Cited

U.S. PATENT DOCUMENTS

| | | | |
|---|---|---|---|
| 2002/0010425 | A1 | 1/2002 | Guo et al. |
| 2003/0171721 | A1 | 9/2003 | Enomoto et al. |
| 2004/0044266 | A1 | 3/2004 | Siess et al. |
| 2004/0267202 | A1 | 12/2004 | Potter |
| 2005/0010238 | A1 | 1/2005 | Potter et al. |
| 2005/0033239 | A1 | 2/2005 | Argentine |
| 2006/0145116 | A1 | 7/2006 | Rickerd et al. |
| 2009/0012476 | A1 | 1/2009 | Catlin |
| 2009/0023429 | A1 | 1/2009 | Naaman et al. |
| 2009/0234290 | A1 | 9/2009 | Fisher et al. |
| 2010/0100044 | A1 | 4/2010 | Ye et al. |
| 2010/0179480 | A1 | 7/2010 | Sugiki et al. |
| 2010/0241083 | A1 | 9/2010 | Fisher et al. |
| 2011/0152763 | A1 | 6/2011 | Bishop et al. |
| 2012/0221024 | A1 | 8/2012 | Sutton et al. |
| 2013/0046241 | A1 | 2/2013 | Okamura et al. |
| 2016/0008803 | A1 | 1/2016 | Jost |
| 2020/0241083 | A1 | 7/2020 | Franke |

FOREIGN PATENT DOCUMENTS

| | | | |
|---|---|---|---|
| CN | 102811760 | B | 7/2015 |
| JP | H0187746 | U | 6/1989 |
| JP | H05028348 | U | 4/1993 |
| JP | H0639011 | A | 2/1994 |
| JP | H06154336 | A | 6/1994 |
| JP | 2610725 | B2 | 5/1997 |
| JP | H10127775 | A | 5/1998 |
| JP | H114893 | A | 1/1999 |
| JP | H11128359 | A | 5/1999 |
| JP | 2001327608 | A | 11/2001 |
| JP | 2003520652 | A | 7/2003 |
| JP | 3463972 | B2 | 11/2003 |
| JP | 2004208853 | A | 7/2004 |
| JP | 2007533341 | A | 11/2007 |
| JP | 2011510686 | A | 4/2011 |
| JP | 2011130846 | A | 7/2011 |
| JP | 2011212417 | A | 10/2011 |
| JP | 4940526 | B2 | 3/2012 |
| JP | 2016510686 | A | 4/2016 |
| JP | 2018510515 | A | 4/2018 |
| WO | 0154763 | A2 | 8/2001 |
| WO | 2005016180 | A2 | 2/2005 |
| WO | 2009002828 | A2 | 12/2008 |
| WO | 2009038727 | A1 | 3/2009 |
| WO | 2013005607 | A1 | 1/2013 |
| WO | 2016055368 | A1 | 4/2016 |
| WO | 2016160778 | A1 | 10/2016 |
| WO | 2020135607 | A1 | 7/2020 |

OTHER PUBLICATIONS

Office Action from corresponding Korean Patent Application No. 10-2018-7008328 dated Aug. 21, 2023 (15 pp.).

Extended European Search Report for EP Application No. 20201854.5 dated Oct. 29, 2020 (10 pages).

International Search Report dated Nov. 10, 2016 for International Application No. PCT/US2016/048459, filed Aug. 24, 2016.

Notice of Reasons for Revocation from corresponding Japanese Patent No. 6956069 dated Sep. 9, 2022 (32 pages).

Office Action from corresponding Japanese Application No. 2021-163179 dated Oct. 24, 2022 (8 pages).

Office Action in corresponding Australian Patent Application No. 2021200363 dated Apr. 26, 2022 (6 pp.).

Office Action issued in corresponding Indian Application No. 201817008180 dated Feb. 2, 2021 (6 pages).

Office Action issued in corresponding Israeli Application No. 257687 dated Mar. 1, 2021 (4 pages). No translation provided.

Office Action issued in corresponding Japanese Application No. 2018-510515 dated Aug. 31, 2020 (10 pages).

Preliminary Office Action issued in corresponding Brazilian Patent Application No. BR1120180037370 dated Jun. 9, 2020.

Supplementary EP Search Report, EP 16 84 0060 dated Apr. 16, 2019.

Office Action corresponding to Canadian Patent Application No. 2,996,531 dated Jun. 8, 2023 (3 pp.).

Office Action from corresponding Japanese Patent Application No. 2024-091708 dated Jan. 29, 2025 (4 pp.).

Office Action from corresponding Thailand Patent Application No. 1801001065 dated Mar. 11, 2025 (4 pp.).

Office Action from corresponding Australian Patent Application No. 2023206099 dated Nov. 1, 2024 (3 pp.).

Office Action from corresponding Korean Patent Application No. 10-2024-7016669 dated Sep. 20, 2024 (14 pp.).

Notice of Reasons for Refusal in Japanese Patent Application No. 2024-091708, dated Oct. 1, 2025 (9 pp.).

* cited by examiner

HEMOSTATIC VALVE FOR MEDICAL DEVICE INTRODUCER

CROSS-REFERENCE TO RELATED APPLICATIONS

This application is a continuation of U.S. patent application Ser. No. 16/784,329, filed on Feb. 7, 2020, now allowed, which application is a continuation of U.S. patent application Ser. No. 15/245,982, filed on Aug. 24, 2016, now U.S. Pat. No. 10,576,258, which application claims the benefit of U.S. Provisional Patent Application No. 62/209,288, filed on Aug. 24, 2015, all of which are hereby incorporated herein by reference in their entirety.

BACKGROUND OF THE INVENTION

Patients with cardiac ailments are sometimes treated with heart pumps adapted to be inserted into the heart through adjoining blood vessels and configured to assist the natural cardiac pump function or to replace natural cardiac pump function by a continuous pumping operation.

In one common approach, an introducer sheath is used to gain vascular access prior to insertion of a medical device such as a heart pump. The introducer sheath includes a hemostatic valve that prevents blood leakage from the proximal end of the introducer sheath upon insertion of the introducer sheath into a blood vessel. The hemostatic valve should prevent excessive blood leakage when no objects are present in the valve or when guidewires, catheters, blood pumps, or other objects are inserted through the valve. One of the primary causes of excess leakage in an introducer sheath is damage to or perforation of the hemostatic valve.

BRIEF SUMMARY OF THE INVENTION

In one common approach, an introducer sheath is used to gain vascular access prior to insertion of a medical device such as a heart pump. The introducer sheath includes a hemostatic valve that prevents blood leakage from the proximal end of the introducer sheath upon insertion of the introducer sheath into a blood vessel. The hemostatic valve should prevent excessive blood leakage when no objects are present in the valve or when guidewires, catheters, blood pumps, or other objects are inserted through the valve. One of the primary causes of excess leakage in an introducer sheath is damage to or perforation of the hemostatic valve. The guide may be formed from the hemostatic valve or as a separate element. The systems, methods, and devices described herein reduce or eliminate the risk of valve perforation during insertion of medical devices (e.g., heart pumps), guidewires, dilators, or other objects by guiding inserted objects toward the center of the hemostatic valve. This can reduce or prevent blood leakage through the hemostatic valve.

The hemostatic valve will additionally simplify user interaction with the introducer sheath. Current systems, methods, and devices may require a pre-requisite level of experience or attention from a user during a preparation phase, or during insertion of medical devices (e.g., heart pumps), guidewires, dilators, or other objects. However the proposed introducer sheath would improve ease of use with the system without requiring such pre-requisite levels of experience or attention from a user. Additionally, performance of the introducer sheath would be independent of the location on the hemostatic valve at which medical devices (e.g., heart pumps) are inserted. This minimizes human factor considerations and accommodates a wider range of use conditions.

In one aspect, an introducer for insertion of a medical device into a patient's vasculature includes an elongate introducer body, a hub, and a hemostatic valve. The elongate introducer body includes a longitudinal axis, a proximal region, a distal region, and an inner lumen. The hub is coupled to the proximal region of the introducer body. The hemostatic valve is disposed within the hub and forms a liquid-tight seal across the inner lumen. The hemostatic valve includes a guide configured to guide an object towards the center of the valve during insertion of the object. The guide may be a funnel. In some implementations, the hemostatic valve has a proximal surface and a distal surface, and the funnel is defined by sloped regions of the proximal surface of the hemostatic valve. The funnel may be separate from the hemostatic valve. The sloped regions may be angled about 30°, about 45°, about 60°, or greater relative to the plane perpendicular to the longitudinal axis of the introducer body. In certain implementations, the proximal surface includes a flat central region that is substantially perpendicular to the longitudinal axis of the elongate introducer body. The flat central region may have a diameter of about 3 mm or less. In some implementations, the introducer is configured to part along a parting surface substantially parallel to the longitudinal axis of the introducer body. In certain implementations, the hemostatic valve is configured to part along a parting surface substantially parallel to the longitudinal axis of the introducer body. The hemostatic valve may include a central void that reduces the stiffness of the center of the hemostatic valve.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, method, and devices described. To provide an overall understanding of the systems, method, and devices described.

The apparatus described herein provides an introducer sheath and a hemostatic valve for percutaneous insertion of a heart pump. The introducer sheath includes a guide and a hemostatic valve. The introducer sheath guides an object towards the center of the hemostatic valve to reduce the risk of inadvertently puncturing the hemostatic valve during insertion of the object (e.g., a heart pump). The guide may be formed from the hemostatic valve or as a separate element. The systems, methods, and devices described herein thus reduce or eliminate the risk of valve perforation during insertion of medical devices (e.g., heart pumps), guidewires, dilators, or other objects. This can reduce or prevent blood leakage through the hemostatic valve.

Figure 1:
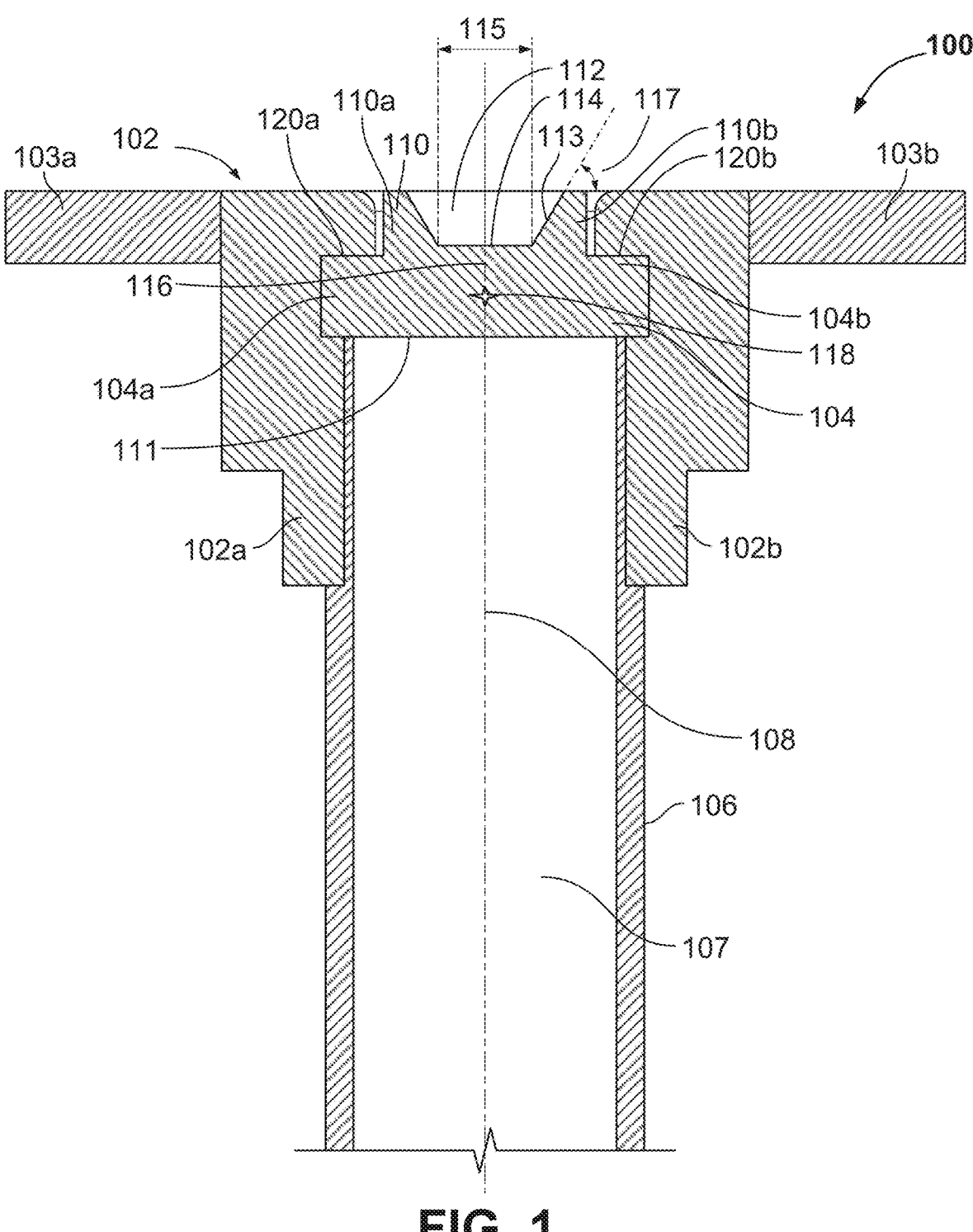
FIGS. 1 and 2 show cross-section views of an introducer assembly including a funnel valve according to certain embodiments.
Figure 2:
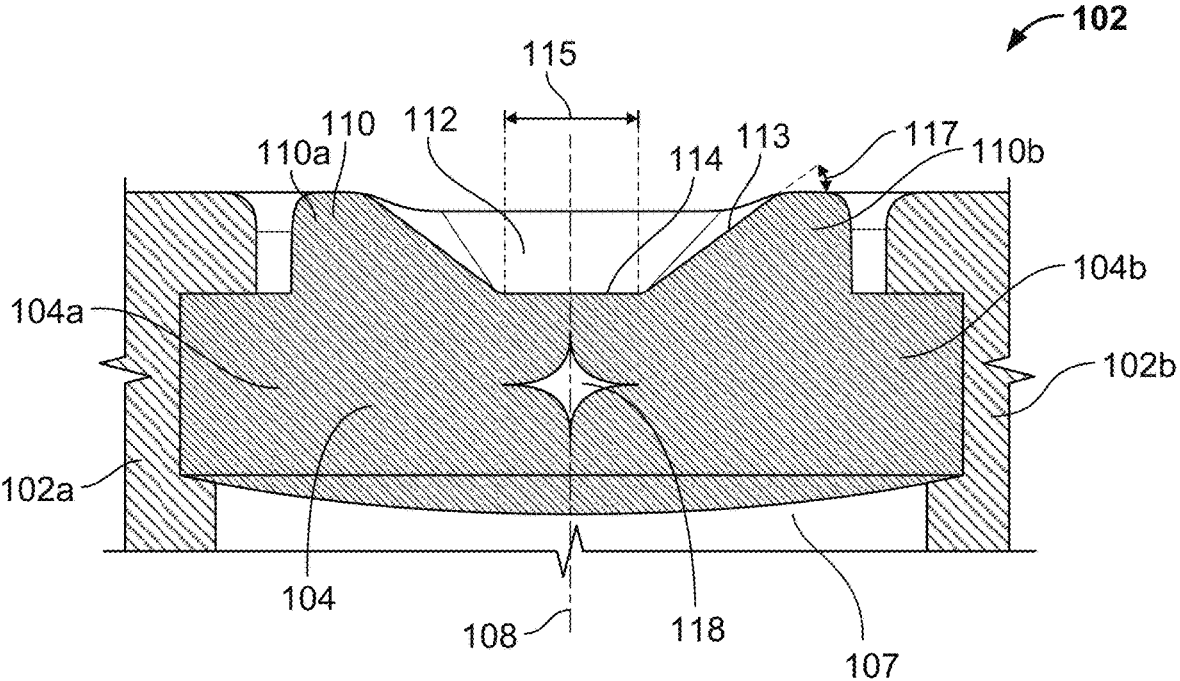

FIGS. 1 and 2 show cross-section views of an introducer assembly 100 including a funnel valve according to certain embodiments. The introducer assembly 100 includes an elongate introducer body 106, a hub 102, and a hemostatic valve 104. The elongate introducer body 106 has an inner lumen 107 and a longitudinal axis 108. The hub 102 includes a first hub portion 102a, a second hub portion 102b, a first wing 103a, and a second wing 103b. The hemostatic valve 104 includes a first hemostatic valve portion 104a, a second hemostatic valve portion 104b, a guide 110, a distal surface 111, a proximal surface 112, a sloped region 113, a flat region 114, an outer region 120, a parting surface 116, and a central void 118.

The hemostatic valve 104 creates a liquid tight seal across the inner lumen 107 of the elongate introducer body 106. The guide 110 of the hemostatic valve 104 guides objects inserted into the hemostatic valve 104 such that the objects are guided to the central flat region 114. This reduces the risk of inadvertently puncturing the hemostatic valve 104 during insertion of an object (e.g., a heart pump). The guide 110 includes a first guide portion 110a and a second guide portion 110b. The guide 110 is formed by the proximal surface 112 of the hemostatic valve 104. The proximal surface 112 includes the sloped region 113, which defines the funneled shape of the guide 110, and the central flat region 114. The sloped region 113 is angled relative to the central flat region 114 by a funnel angle 117. The funnel angle 117 is about 30°. In some implementations, the funnel angle is about 10°, 15°, 20°, 25°, 30°, 35°, 40°, 45°, 50°, 55°, 60°, 60°, 70°, 75°, 80°, 85°, or any other suitable angle. The funnel angle 117 is suitably steep to guide inserted objects towards the central flat region 114. The funnel angle 117 is shown as substantially constant in FIG. 1, but the person of ordinary skill will appreciate that the funnel angle can flare or vary over the length of the sloped region 113. The central flat region 114 of the hemostatic valve has a diameter 115. The diameter 115 may be 1 cm, 5 mm, 4 mm, 3 mm, 2 mm, 1 mm, less than 1 mm, or any other suitable dimension. The guide 110 may have different surface properties, durometer, material, or other properties compared to the remainder of hemostatic valve 104. For example, the guide 110 may be more rigid, tougher, or harder, relative to the remainder of hemostatic valve 104. Although the guide 110 is shown in FIG. 1 as being formed in the hemostatic valve 104, in some embodiments the guide 110 is separate from the hemostatic valve 104. For example, the guide 110 may be formed in the hub 102.

The hemostatic valve 104 is formed of the first hemostatic valve portion 104a and the second hemostatic valve portion 104b. The first hemostatic valve portion 104a and the second hemostatic valve portion 104b are held together by the hub 102 and interface at the parting surface 116. The parting surface 116 separating the first hemostatic valve portion 104a and the second hemostatic valve portion 104b allow the hemostatic valve 104 to be completely separated after insertion of an object. The first hemostatic valve portion 104a is connected to the first hub portion 102a at the outer region 120a, and the second hemostatic valve portion 104b is connected to the second hub portion 102b at the outer region 120b. The connection between the hub 102 and the hemostatic valve 104 may be an interference fit, an adhesive bond, a connection by a mechanical fastener, or any other suitable connection. The parting surface 116 also defines a central void 118. The central void 118 reduces the stiffness of the hemostatic valve 104 in the central flat region 114. This may allow the valve to easily give or to deform in the central flat region 114 when an object is inserted. This may also allow the hemostatic valve 104 to form a double seal against an object inserted through the hemostatic valve 104. A double seal may provide redundancy, thereby decreasing the risk of valve leakage or failure.

The hemostatic valve 104 is coupled to the elongate introducer body 106 by the hub 102. Similar to the hemostatic valve 104, the hub 102 is split along the parting surface 116 into the first hub portion 102a and the second hub portion 102b. The first and second wings 103a-b provide a lever arm that allows the hub 102 to be manually split into the first hub portion 102a and the second hub portion 102b. This splitting may facilitate the replacement of the introducer assembly 100 with another assembly or sheath during the use of a heart pump. Splitting of the hub 102 also initiates splitting of the elongate introducer body 106 into two parts so that the entire introducer assembly 100 can be removed as will be discussed further in relation to FIGS. 5 and 6. The elongate introducer body 106 has an outer diameter sized for percutaneous insertion. In some implementations, the outer diameter of the elongate introducer body 106 is 10 French (3.33 mm), 11 French (3.67 mm), 12 French (4 mm), 13 French (4.33 mm), 14 French (4.67 mm), 15 French (5 mm), 16 French (5.33 mm), 17 French (5.67 mm), 18 French (6 mm), 19 French (6.33 mm), 20 French (6.67 mm), 21 French (7 mm), or any other suitable diameter.

Figure 3:
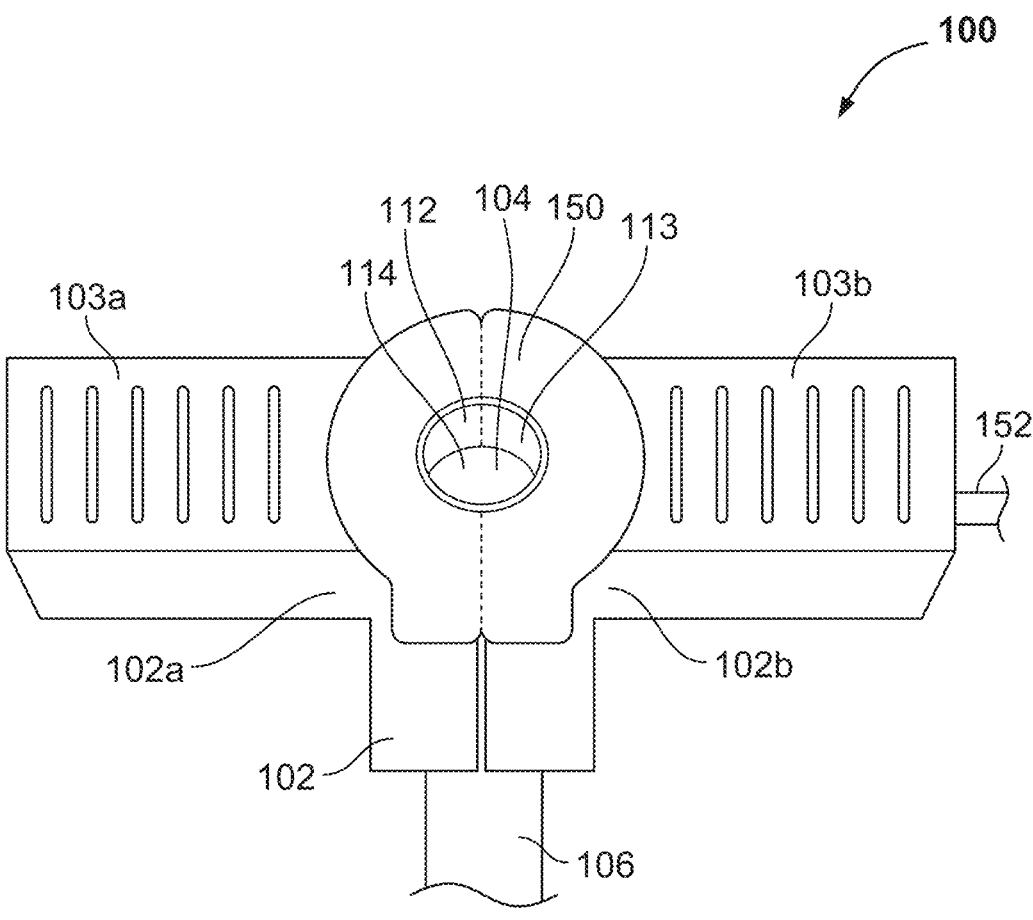
FIG. 3 shows a perspective view of the introducer assembly of FIGS. 1 and 2.

FIG. 3 shows a perspective view of the introducer assembly of FIGS. 1 and 2. The introducer assembly 100 includes the elongate introducer body 106, the hub 102, the hemostatic valve 104, a reinforcing ring 150, and a fluid line 152. The hub 102 includes the first hub portion 102a, the second hub portion 102b, the first wing 103a, and the second wing 103b. The hemostatic valve 104 includes the proximal surface 112 having the sloped region 113 and the central flat region 114. The fluid line 152 allows the inner lumen 107 (not shown) to be flushed with saline or any other biocompatible fluid to prevent stagnation of blood or blood clot formation in the introducer assembly 100. The reinforcing ring 150 connects the first hub portion 102a and the second hub portion 102b. The reinforcing ring 150 may prevent inadvertent or premature separation of the first and second portions 102a-b of the hub 102. For example, the reinforcing ring 150 may be tougher or stronger than the hub 102 to prevent separation. In some implementations, the reinforcing ring 150 and the tubular sheath body 106 are the only elements of the introducer assembly 100 that are not parted before use. In such an implementation, after the reinforcing ring 150 is separated, no other element holds the first hub portion 102a and the second hub portion 102b together. Separation of the introducer assembly 100 may be more predictable if separation depends on fewer elements.

Figure 4:
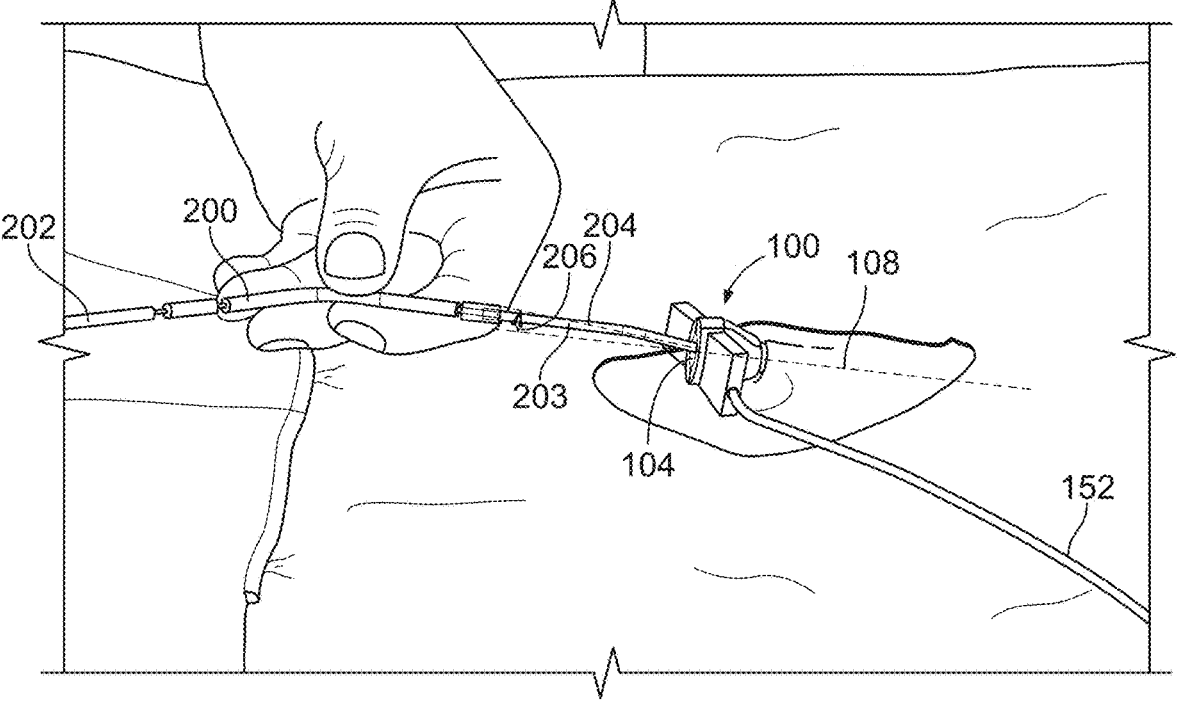
FIG. 4 shows percutaneous insertion of a heart pump using the introducer assembly of FIGS. 1 and 2.

FIG. 4 shows percutaneous insertion of a heart pump assembly 200 using the introducer assembly of FIGS. 1 and 2. The heart pump assembly 200 includes a distal end portion 203 and a supply catheter 202. The sheath assembly 100 includes the hemostatic valve 104 and the fluid supply line 152. The fluid supply line 152 may be used to flush the introducer assembly 100 before during or after insertion of the heart pump assembly 200. In some implementations, the supply catheter 202 of the heart pump assembly 200 includes a flexible drive shaft. The distal end portion 203 of the heart pump assembly 200 is inserted into the introducer assembly 100 along an insertion path 204. The insertion path 204 forms an angle of insertion 206 relative to the longitudinal axis 108 of the introducer assembly 100. The guide (not shown) of the introducer assembly 100 limits the angle of insertion 206 to prevent puncture of the hemostatic valve 104 during insertion of the heart pump assembly 200. The guide may limit the angle of insertion 206 to less than 90°, less than 80°, less than 70°, less than 60°, less than 50°, less than 45°, less than 40°, less than 35°, less than 30°, less than 25°, less than 20°, less than 15°, less than 10°, less than 5°, or to any other suitable angle.

Figure 5:
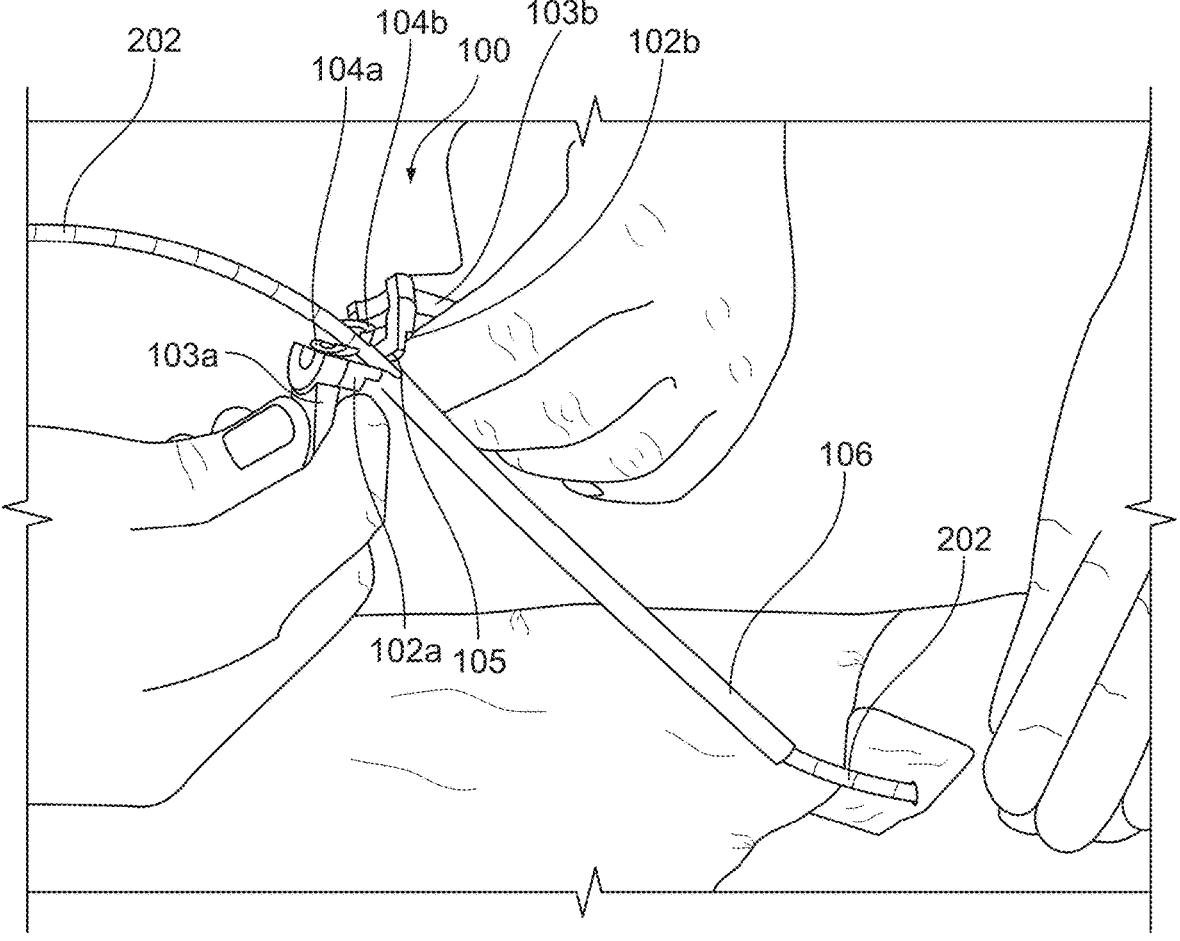
FIGS. 5 and 6 show parting of the introducer assembly of FIGS. 1 and 2.
Figure 6:
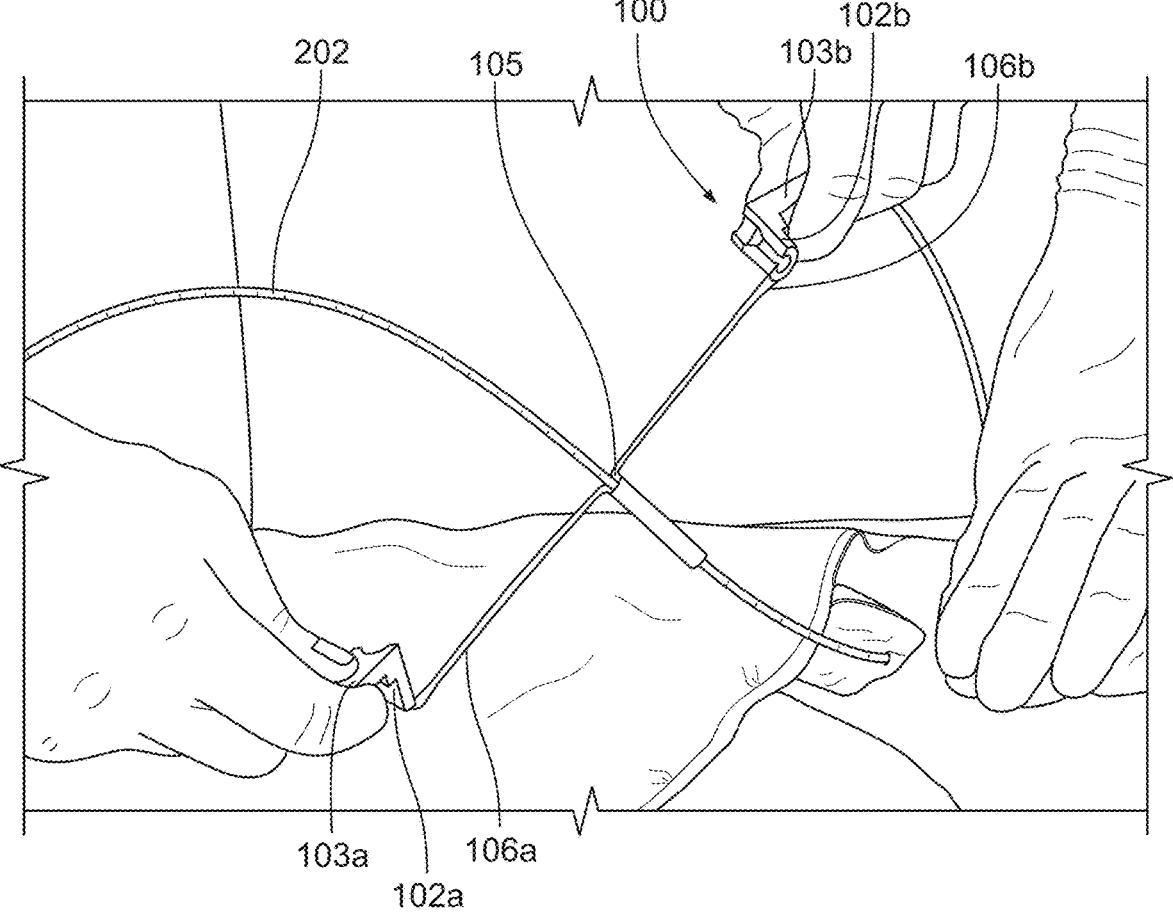

FIGS. 5 and 6 show parting of the introducer assembly of FIGS. 1 and 2. After the heart pump assembly 200 (not shown in FIGS. 5 and 6) has been inserted into the patient, the introducer assembly 100 is separated along a parting surface while remaining on the supply catheter 202. A healthcare professional applies force to the first and second wings 103*a-b* to part (e.g., "peel-away") the introducer assembly 100. This separates the hub 102 into a first hub portion 102*a* and a second hub portion 102*b*. This also separates the hemostatic valve 104 into a first hemostatic valve portion 104*a* and a second hemostatic valve portion 104*b*. This also initiates a crack 105 in the proximal region of the elongate introducer body 106. The crack 105 is advanced by pulling the first huh portion 102*a* and the second hub portion 102*b* farther apart as shown in FIG. 6. This process may continue until the introducer assembly 100 is completely split and separated from the supply catheter 202. This allows another sheath (not shown) to be advanced over the supply catheter 202 into the patient.

Figure 7:
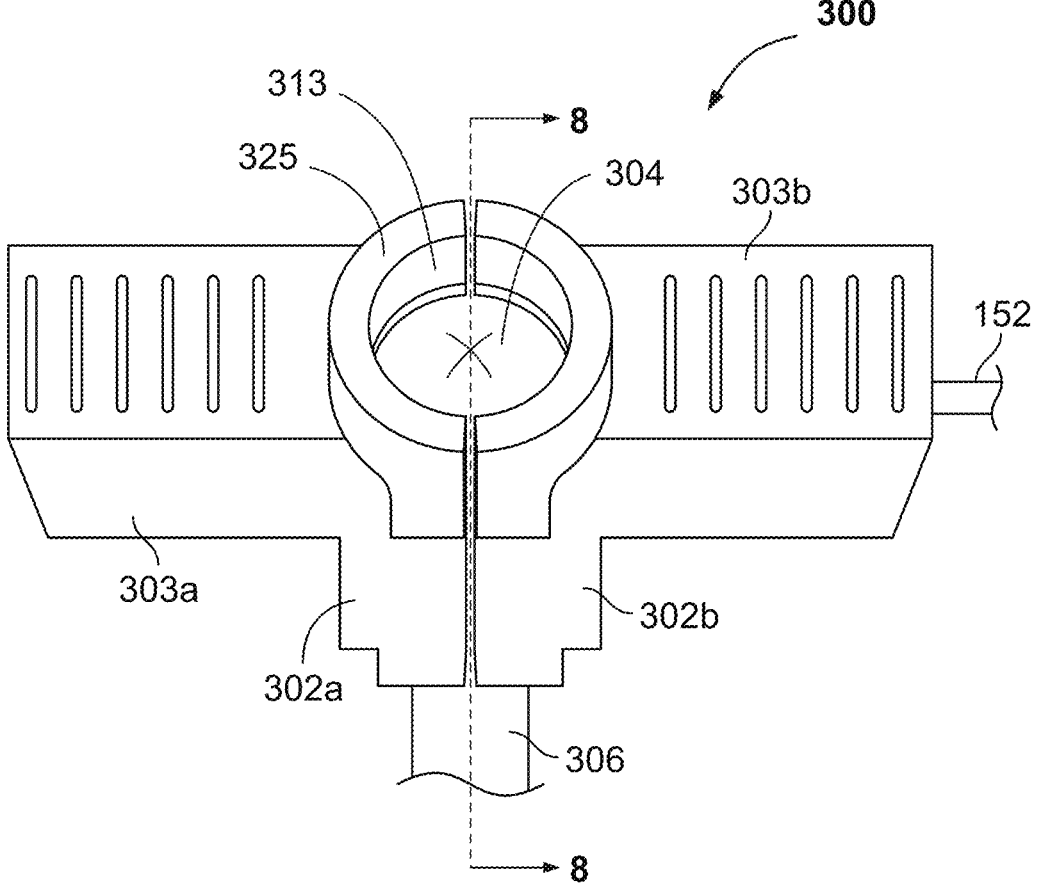
FIGS. 7 and 8 show cross-section views of an alternate introducer assembly including a funnel valve according to certain embodiments.
Figure 8:
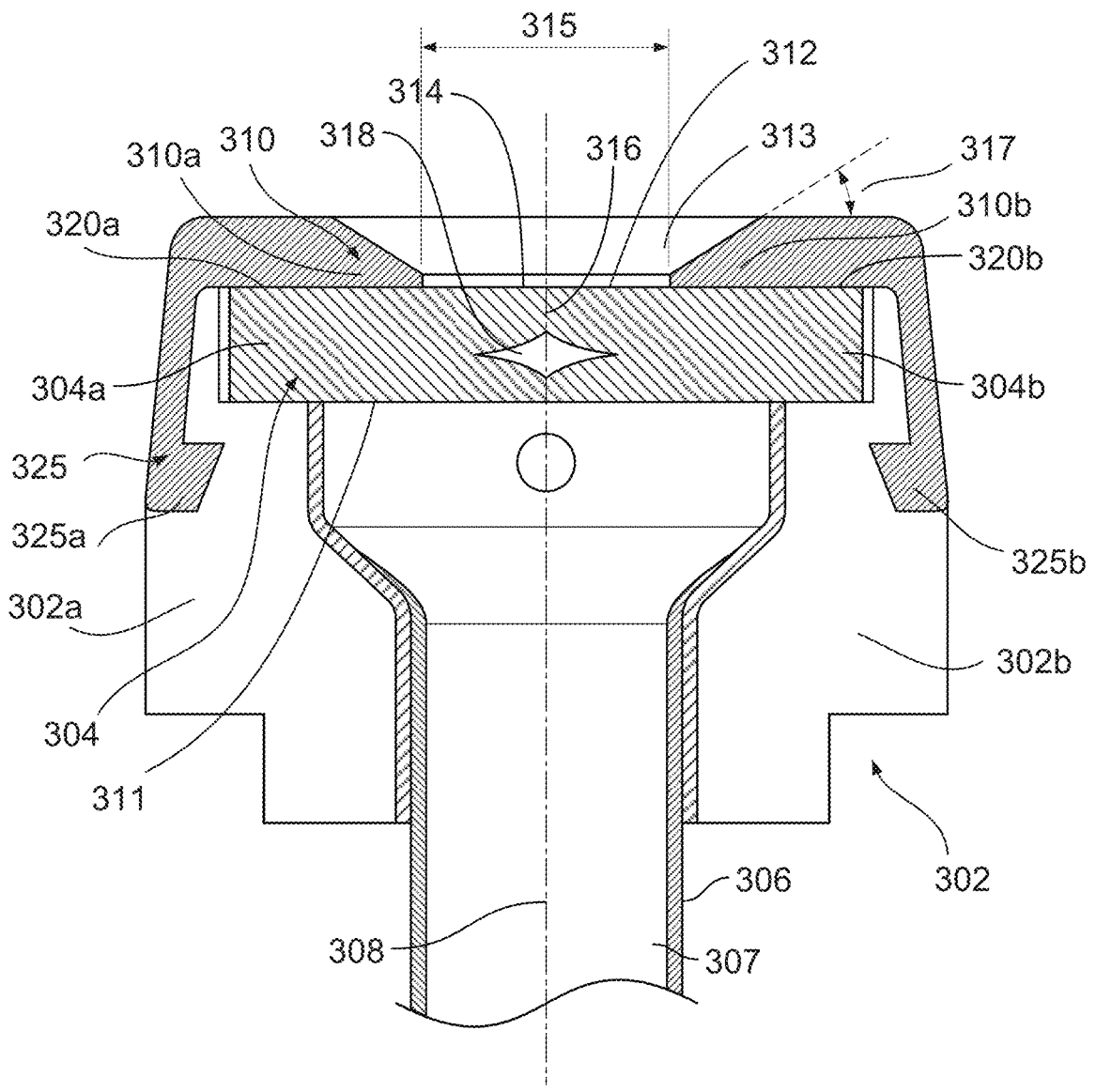

FIGS. 7 and 8 show an alternate introducer assembly 300. The introducer assembly 300 includes an elongate introducer body 306, a hub 302, and a hemostatic valve 304. The elongate introducer body 306 has an inner lumen 307 and a longitudinal axis 308. The hub 302 includes a first hub portion 302*a*, a second hub portion 302*b*, a first wing 303*a*, and a second wing 303*b*. The hemostatic valve 304 includes a first hemostatic valve portion 304*a*, a second hemostatic valve portion 304*b*, a distal surface 311, a proximal surface 312, a parting surface 316, and a central void 318.

In introducer assembly 300, the distal surface 311 and the proximal surface 312 of the hemostatic valve 304 are both substantially flat. A hemostatic valve 304 having a substantially flat profile would less material and complexity to manufacture and implement. The hub 302 also includes a bracket 325 comprising a first bracket portion 325*a* and a second bracket portion 325*b*. A guide 310 is integrally formed with the bracket 325 and comprises a first guide portion 310*a* and second guide portion 310*b* that define a central opening 314. The bracket 325 substantially encompasses the hemostatic valve 304 such that a portion 320*a* and 320*b* of the proximal surface 312 of the hemostatic valve 304 is in contact with the guide portions 310*a* and 310*b* of the bracket 325. In this configuration, the guide 310 exposes a portion of the substantially flat proximal surface 312 of the hemostatic valve 304 in the vicinity of the central opening 314.

The guide 310 includes a sloped region 313, which defines the funneled shape of the guide 310 and the central opening 314, which, in turn, exposes the substantially flat proximal surface 312 of the hemostatic valve 304. The guide 310 is therefore able to guide objects towards the central opening 314 and hence the proximal surface 312 of hemostatic valve 304. The sloped region 313 is angled relative to the exposed flat proximal surface 312 of the hemostatic valve 304 by a funnel angle 317. The funnel angle 317 is about 30°. In some implementations, the funnel angle 317 is about 10°, 15°, 20°, 25°, 30°, 35°, 40°, 45°, 50°, 55°, 60°, 65°, 70°, 75°, 80°, 85°, or any other suitable angle. The funnel angle 317 is suitably steep to guide inserted objects towards the central opening 314 and the flat proximal surface 312 of the hemostatic valve 304. The funnel angle 317 is shown as substantially constant in FIG. 8, but the person of ordinary skill will appreciate that the funnel angle 317 can flare or vary over the length of the sloped region 313. It will also be understood that while the guide 310 in FIG. 8 is shown to have a substantially linear profile, any other suitable profile may be implemented (e.g. a concave downward profile). The central opening 314 of the hemostatic valve has a diameter 315. The diameter 315 may be 1 cm, 5 mm, 4 mm, 3 mm, 2 mm, 1 mm, less than 1 mm, or any other suitable dimension. The bracket 325 may have different surface properties, durometer, material, or other properties compared to the hub 302 or the hemostatic valve 304. For example, the bracket 325 may be more rigid, tougher, or harder, relative to the hub 302 or the hemostatic valve 304.

The hemostatic valve 304 is formed of the first hemostatic valve portion 304*a* and the second hemostatic valve portion 304*b*. The first hemostatic valve portion 304*a* and the second hemostatic valve portion 304*b* are held together by the bracket 325 in the hub 302 and interface at the parting surface 316. The parting surface 316 separating the first hemostatic valve portion 304*a* and the second hemostatic valve portion 304*b* allow the hemostatic valve 304 to be completely separated after insertion of an object. The first hemostatic valve portion 304*a* is connected to the first bracket portion 325*a* at the portion 320*a* of the proximal surface 312 of the hemostatic valve 304, while the second hemostatic valve portion 304*b* is connected to the second bracket portion 325*b* at the portion 320*b* of the proximal surface 312. The connection between the bracket 325 and the hemostatic valve 304 may be an interference fit, an adhesive bond, a connection by a mechanical fastener, or any other suitable connection. The parting surface 316 also defines a central void 318. The central void 318 reduces the stiffness of the hemostatic valve 304 in the vicinity of the central opening 314. This may allow the valve to easily give or to deform in the vicinity of the central opening 314 when an object is inserted. This may also allow the hemostatic valve 304 to form a double seal against an object inserted through the hemostatic valve 304. A double seal may provide redundancy, thereby decreasing the risk of valve leakage or failure.

Similar to the hemostatic valve 304, the hub 302 and bracket 325 are split along the parting surface 316 into the first hub portion 302*a* and the first bracket portion 325*a*, and the second hub portion 302*b* and the second bracket portion 325*b*. The first and second wings 303*a-b* provide a lever arm that allows the hub 302 and guide 310 to be manually split into the first hub portion 302*a* the first bracket portion 325*a*, and the second huh portion 302*b* and the second bracket portion 325*b*. This splitting may facilitate the replacement of the introducer assembly 300 with another assembly or sheath during the use of a heart pump. Splitting of the hub 302 also initiates splitting of the elongate introducer body 306 into two parts so that the entire introducer assembly 300 can be removed as previously discussed in relation to FIGS. 5 and 6.

The reinforcing ring 150 discussed in relation to FIGS. 1 to 3 can also be used with the introducer assembly 300 to connect the hub portions 302*a-b* and the bracket portions 325*a-b*. The reinforcing ring 150 may prevent inadvertent or premature separation of the first and second portions 302*a-b* of the hub 302 and the first and second portions 325*a-b* of the bracket 325. For example, the reinforcing ring 150 may be tougher or stronger than the hub 302 to prevent separation. In some implementations, the reinforcing ring 150 and the tubular sheath body 306 are the only elements of the introducer assembly 300 that are not parted before use. In such an implementation, after the reinforcing ring 150 is separated, no other element holds the first and second hub portions 302*a-b* and the first and second bracket portions 325 *a-b* together.

In a further alternate implementation, the guide portion 310 may be located in the reinforcing ring 150.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. An introducer for insertion of a medical device into a patient's vasculature, the introducer comprising:
   an elongate introducer body having a longitudinal axis, a proximal region, a distal region, and an inner lumen;
   a hub coupled to the proximal region of the introducer body; and
   a hemostatic valve disposed within the hub and forming a liquid-tight seal across the inner lumen,
   wherein the hemostatic valve is a unitary structure comprising a valve portion and a guide portion, the guide portion configured to direct an object toward a central region of the hemostatic valve,
   wherein a rigidity, toughness, or hardness of the guide portion is greater than a rigidity, toughness, or hardness of the valve portion,
   wherein the valve portion comprises a central void that reduces a stiffness of the central region of the hemostatic valve, wherein the central void is disposed between a distal surface and proximal surface of the valve portion, and
   wherein the central void is enclosed by material of the valve portion.

2. The introducer of claim 1, wherein the guide portion is defined by a sloped region to the proximal surface and the valve portion comprises the central region.

3. The introducer of claim 2, wherein the central region is flat and substantially perpendicular to the longitudinal axis of the introducer body.

4. The introducer of claim 3, wherein the flat central region has a diameter of about 3 mm or less.

5. The introducer of claim 2, wherein the sloped region is angled about 30° or greater relative to a plane perpendicular to the longitudinal axis of the introducer body.

6. The introducer of claim 2, wherein the sloped region is angled about 60° or greater relative to a plane perpendicular to the longitudinal axis of the introducer body.

7. The introducer of claim 2, wherein the sloped region is a funnel.

8. The introducer of claim 1, wherein the introducer is configured to part along a parting surface substantially parallel to the longitudinal axis of the introducer body.

9. The introducer of claim 1, wherein the hemostatic valve is configured to part along a parting surface substantially parallel to the longitudinal axis of the introducer body.

10. The introducer of claim 1, wherein the hub and the hemostatic valve are configured to part together.

11. The introducer of claim 1, wherein the central void is configured such that the hemostatic valve forms a double seal against the object when the object is inserted through the hemostatic valve.

12. The introducer of claim 1, wherein the guide portion is formed as part of the hemostatic valve.

13. An introducer for insertion of a medical device into a patient's vasculature, the introducer comprising:
   an elongate introducer body having a longitudinal axis, a proximal region, a distal region, and an inner lumen;
   a hub coupled to the proximal region of the introducer body; and
   a hemostatic valve disposed within the hub and forming a liquid-tight seal across the inner lumen,
   wherein the hemostatic valve is a unitary structure comprising a valve portion and a guide portion, the guide portion configured to direct an object toward a central region of the hemostatic valve,
   wherein a rigidity, toughness, or hardness of the guide portion is greater than a rigidity, toughness, or hardness of the valve portion,
   wherein the valve portion comprises a central void that reduces a stiffness of the central region of the hemostatic valve, wherein the central void is disposed between a distal surface and proximal surface of the valve portion, and
   wherein the central void is configured such that the hemostatic valve forms a double seal against the object when the object is inserted through the hemostatic valve.

* * * * *